(12) United States Patent
Rehkemper

(10) Patent No.: US 7,168,121 B2
(45) Date of Patent: *Jan. 30, 2007

(54) ELECTRIC FOLDING TOOTHBRUSH

(75) Inventor: Steven Rehkemper, Chicago, IL (US)

(73) Assignee: Rehco, LLC, Chicago, IL (US)

( * ) Notice: Subject to any disclaimer, the term of this patent is extended or adjusted under 35 U.S.C. 154(b) by 383 days.

This patent is subject to a terminal disclaimer.

(21) Appl. No.: 10/781,960

(22) Filed: Feb. 20, 2004

(65) Prior Publication Data

US 2006/0005330 A1    Jan. 12, 2006

(51) Int. Cl.
*A46B 13/02* (2006.01)
(52) U.S. Cl. .......................................... 15/22.1; 15/28
(58) Field of Classification Search ............... 15/22.1, 15/28; 30/45
See application file for complete search history.

(56) References Cited

U.S. PATENT DOCUMENTS

| | | | | |
|---|---|---|---|---|
| 4,364,104 A | * | 12/1982 | Holahan et al. ............ 362/223 |
| 4,598,437 A | * | 7/1986 | Ernest et al. .............. 15/176.1 |
| 5,206,994 A | * | 5/1993 | Lin ................................ 30/47 |
| 5,465,488 A | * | 11/1995 | Yaw et al. ...................... 30/41 |
| 6,481,104 B1 | * | 11/2002 | Parker et al. ................... 30/45 |
| 2001/0042279 A1 | * | 11/2001 | Heavenor .................. 15/167.1 |
| 2002/0124333 A1 | * | 9/2002 | Hafliger et al. .............. 15/22.1 |

* cited by examiner

*Primary Examiner*—Randall Chin

(57) ABSTRACT

An electric folding toothbrush in accordance with the present invention includes a handle and a power supply contained within the handle, an arm movably joined to the handle and having bristles disposed at one end thereof, a motor mechanism contained within the arm and operable to move the bristles when activated, and includes the ability to supply power to the motor mechanism when the toothbrush is in an outstretched position. The ability to supply power to the motor mechanism is accomplished with a first electrical contact in communication with the power supply and positioned in the handle, and a second electrical contact in communication with the motor mechanism and positioned in the arm such that when the arm and the handle are in the outstretched position the first and second electrical contacts make an electrical connection such that power from the power supply operates the motor mechanism.

8 Claims, 3 Drawing Sheets

ELECTRIC FOLDING TOOTHBRUSH

FIELD OF THE INVENTION

The present invention relates to various folding toothbrushes and particularly to a folding toothbrush that include bristles that move, vibrate, or rotate.

BACKGROUND OF THE INVENTION

Toothbrushes are well known in the industry. Moreover, folding and compact toothbrushes are also well known. Numerous patents have issued throughout the years to cover various improvements and novel features in the toothbrush industry. Some of these patents include: U.S. Pat. No. 5,735,298 directed to a tri-fold multipurpose toothbrush that has various head attachments; U.S. Pat. No. 4,979,258 directed to a children's folding toothbrush that is shaped like an airplane; U.S. Pat. No. 2,353,963 directed to a toothbrush that included a cavity to hold the bristles when the toothbrush was folded; and U.S. Pat. No. 5,382,107 directed to a toothbrush that locks in the folded position and includes a spring that normally biases the head portion away from the handle portion, such that when the folded toothbrush is unlocked the spring acts to move the toothbrush into the unfolded position.

However, with the increase in popularity of electric toothbrushes that provide for bristles that move (oscillate, vibrate, or rotate) the prior art and the industry lack the ability to provide the user with a compact electric toothbrush. Especially when a person travels, the user will typically take a folding or compact toothbrush, because electric toothbrushes are bulky. The user thus loses the ability to have a compact folding travel toothbrush that still provides moving bristles.

The present invention overcomes these shortcomings by providing a folding toothbrush that includes means for moving the bristles.

SUMMARY OF THE INVENTION

In accordance with the present invention a folding electric toothbrush is included. The toothbrush contains a handle and an arm movably joined to the handle, which includes bristles disposed at one end. The toothbrush has a power supply contained within the handle and a mechanical means contained within the arm and operated by the power supply to move the bristles when the mechanical means is activated. The activation of the mechanical means is obtained when the toothbrush is in an unfolded position. While the activation may be achieved in many different ways, the preferred manner includes a first electrical contact in communication with the power supply and positioned in the handle, and a second electrical contact in communication with the motor mechanism and positioned in the arm such that when toothbrush is in the unfolded position the first and second electrical contacts make an electrical connection whereby power from the power supply is able to operate the motor mechanism.

In another aspect of the invention, when the toothbrush is in a folded position, the electrical connection between the first and second electrical contacts is broken such that the mechanical means becomes disabled. The manner in which the mechanical means moves the bristles is defined by having a motor mechanism that rotates an axle that has weight secured in an offset position, such that when the offset weight is spun the end of the arm oscillates causing the bristles vibrate. In addition thereto, the handle preferably includes a cavity for receiving the arm and the bristles therein when the toothbrush is in a folded position.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein.

DETAILED DESCRIPTION OF THE EMBODIMENTS

Figure 1:
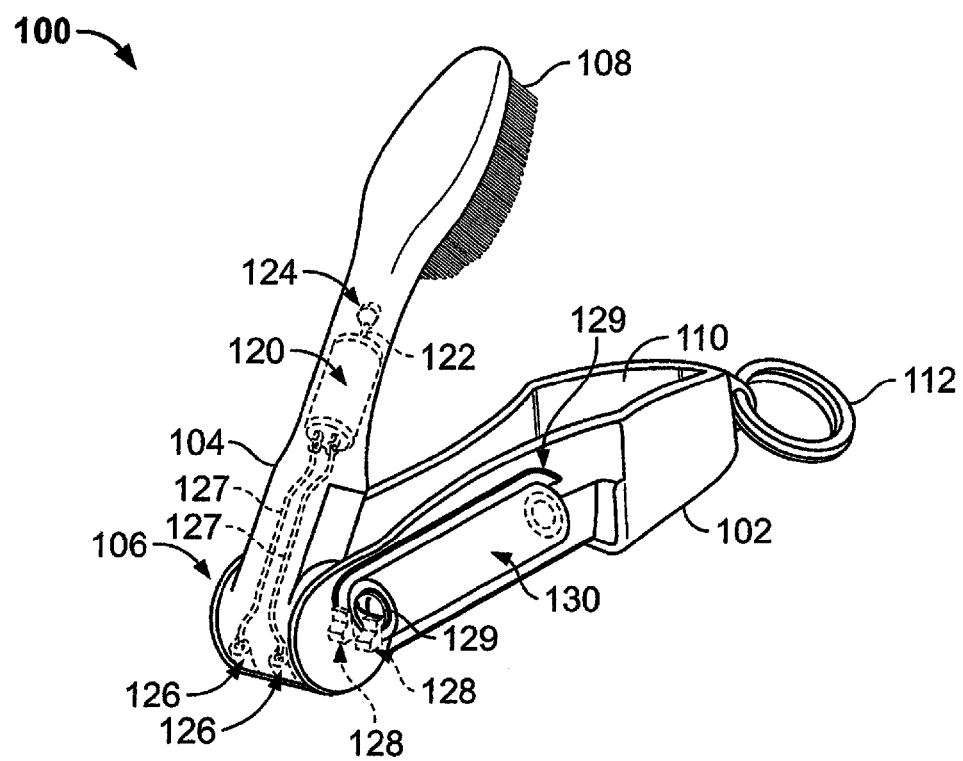
FIG. 1 is a perspective view of an electric folding toothbrush illustrating the components through the outside cover of the toothbrush and illustrating the toothbrush in a partially folded position.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Figure 2:
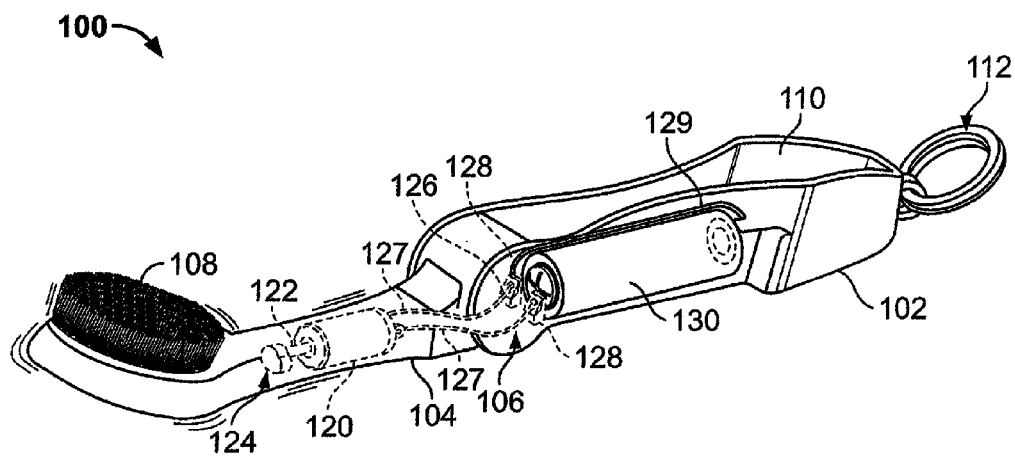
FIG. 2 is a perspective view of the toothbrush in FIG. 1 illustrating the toothbrush in an unfolded position.

Referring now to FIG. 1, an electric folding toothbrush is illustrated and generally referenced to as 100. The toothbrush includes a handle section 102 that a user grasps during use of the toothbrush 100. An arm section 104 is moveably attached to one end of the handle section 102. As illustrated in FIGS. 1 and 2, the pivotal region 106 permits the arm section 104 and the handle section 102 to pivot about the region in such a manner that the toothbrush 100 may move from a substantially folded position to a substantially prone position. Secured to the other end of the arm is a plurality of bristles 108.

Figure 3:
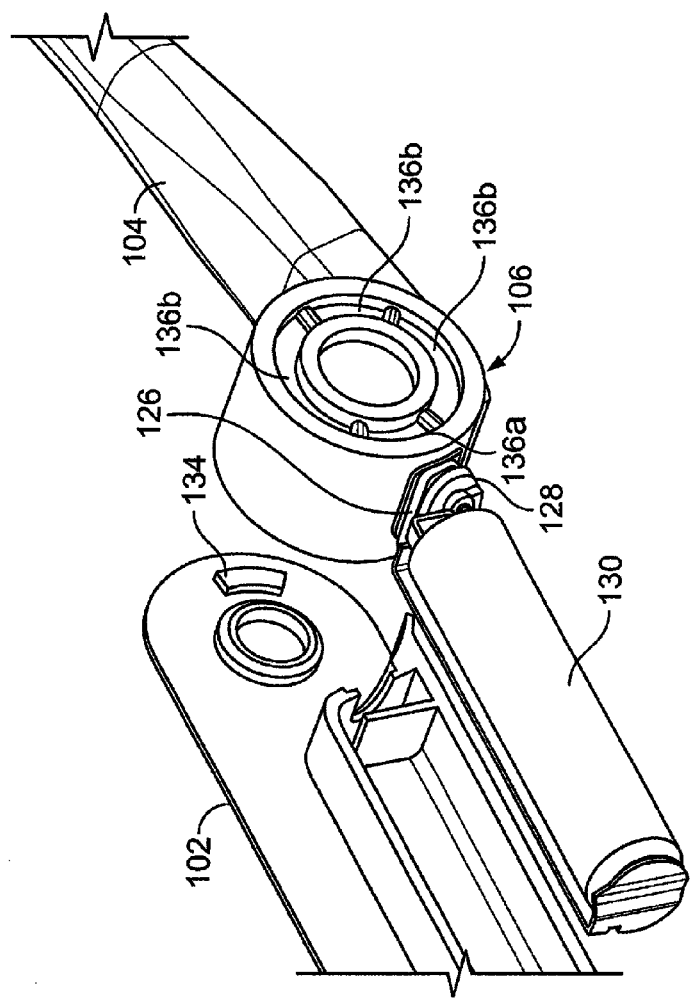
FIG. 3 is an enlarged perspective view of a mechanism that holds the toothbrush in an unfolded position.

As illustrated in FIGS. 1–3 the handle 102 preferably includes an end with a pair of opposing sides to define a gap therebetween. The arm 104 is movably joined between the opposing sides of the end of the handle 102, to define a moveable junction there between.

While the shape of the toothbrush 100 is not critical to the invention, the present invention includes a handle section 102 that has a cavity 110 that is sized to receive the plurality of bristles 108 and the arm section 104 when the toothbrush 100 is in a folded position. This permits the toothbrush to be extremely compact, well suited for the travel industry.

The toothbrush includes a mechanical means to move the bristles 108. The mechanical means is preferably a motor 120 contained within the arm that rotates an axle 122 that includes a weight 124 that is secured to the axle 122 in an offset position. When the motor 120 is activated the offset weight 124 spins causing the bristles 108 to vibrate. Other means for moving the bristles contemplated by this invention and covered by the aforementioned claims include having a motor that drives a gear train, which rotates or oscillates the bristles, such means are well known in the electric toothbrush industry.

To operate the present invention, a set of motor contacts 126 in electrical communication 127 with the motor will make an electrical connection with a set of power contacts 128 that are in electrical communication 129 with a power supply 130 or a battery. The toothbrush 100 houses the set of motor contacts 126 in the arm 104 about the pivotal region 106 and houses the set of power contacts 128 in the handle 102 also about the pivotal region 106. The two sets of contacts 126 and 128 are externally exposed such that when the toothbrush is in a substantially prone position, the two sets of contacts 126 and 128 make the electrical connection, which provides power to the motor 120 (FIG. 2). In addition, to deactivate the motor 120 or break the electrical connection, the toothbrush 100 is moved from the substantially prone position to a folded position (FIG. 1).

Referring now to FIG. 3, the toothbrush 100 also includes a means to maintain the toothbrush 100 in an unfolded and folded position. The means to maintain the toothbrush 100 in a specific position is achieved by providing a pair of opposing detents 134 on the inside portion of the handle section 102 about the pivoting region 106 (only one of the detents 134 is shown). The detents 134 slide into recesses on the arm section 104 also about the pivoting region 106. When the toothbrush 100 is in an unfolded position and electrical contact is made between the two sets of contacts 126 and 128, the detents 134 are positioned in the first recess 136*a*. This helps to maintain the electrical connection during use of the toothbrush 100. When the toothbrush 100 is moved out of the unfolded position, by pivoting the handle section 102 and arm section 104 towards each other, the detents 134 are moved out of the first recess 136*a* and into the secondary recesses 136*b*. While in this position, the detents 134 help prevent the toothbrush 100 from accidentally moving into the unfolded position, and thus inadvertently activating the toothbrush 100.

In addition, one end of the toothbrush 100 may also include a key ring 112 or other external attachment means for attaching the toothbrush 100 to the user's keys or for attaching the toothbrush to a zipper defined on a travel bag. This would help prevent the user from misplacing or forgetting the toothbrush 100.

From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

I claim:

1. A folding toothbrush comprising:
   a handle;
   an arm movably joined to said handle and having bristles disposed at one end thereof;
   a power supply contained within the handle;
   a mechanical means contained within the arm and operated by said power supply to create movement of the bristles when said mechanical means is activated;
   wherein the power supply includes a first electrical contact and the mechanical means includes a second electrical contact and when the toothbrush is in an unfolded position the first electrical contact makes an electrical connection with the second electrical contact to power the mechanical means; and
   a means to maintain the toothbrush in said unfolded position, wherein the means to maintain the toothbrush in said unfolded position includes a detent fixed on the handle about a region defined as where the arm is joined to the handle, said detent moves in relation to a first recess, of a plurality of recesses fixed on the arm about said region.

2. The toothbrush of claim 1, wherein when the toothbrush is in a folded position, the electrical connection between the first and second electrical contacts is broken such that the mechanical means becomes disabled.

3. The toothbrush of claim 2, wherein the mechanical means to create movement of the bristles includes a motor mechanism and an offset weight that is spun about an axle that is rotated by the motor mechanism.

4. The toothbrush of claim 1, wherein said handle includes a cavity for receiving said arm and said bristles therein when the toothbrush is in a folded position.

5. A toothbrush comprising:
   a handle having a power supply contained therein, and having an end with a pair of opposing sides positioned to define a gap therebetween;
   an arm movably joined between said opposing sides of said end of the handle, to define a moveable junction there between, and having bristles disposed at one end of said arm;
   a motor mechanism contained within the arm and operable to move said bristles when activated; and
   a means for supplying power to the motor mechanism when the toothbrush is in an outstretched position;
   a region defined about the moveable junction of the arm and the handle;
   a detent fixed on an inside area defined on each opposing side of said handle about said region; and
   corresponding first recesses, of a plurality of corresponding recesses, fixed on an outside area defined on either side of said arm about said region;
   wherein the toothbrush is maintained in an outstretched position when said detents move into said corresponding first recesses.

6. The toothbrush of claim 5, wherein the means for supplying power to the motor mechanism when the toothbrush is in an outstretched position includes a first electrical contact in communication with the power supply and positioned in the handle, and a second electrical contact in communication with the motor mechanism and positioned in the arm such that when the arm and the handle are in the outstretched position the first and second electrical contacts make an electrical connection whereby power from the power supply is able to operate the motor mechanism.

7. The toothbrush of claim 6, further comprising a weight attached to an axle that is rotated by the motor mechanism, the weight is positioned on the axle in proximity to the bristles such that when the axle is rotated the spinning weight causes the arm to oscillate such that the bristles vibrate.

8. The toothbrush of claim 5, wherein the toothbrush is maintained in a position other than the outstretched position when the detents are moved into one of the plurality of recesses other than said first recesses.

* * * * *